United States Patent [19]

Cooper et al.

[11] Patent Number: 5,280,014
[45] Date of Patent: Jan. 18, 1994

[54] TREATMENT OF OBESITY AND ESSENTIAL HYPERTENSION AND RELATED DISORDERS

[75] Inventors: Garth J. S. Cooper, Solana Beach, Calif.; Brendan Leighton, Eynsham, England

[73] Assignee: Amylin Pharmaceuticals, Inc., San Diego, Calif.

[21] Appl. No.: 737,794

[22] Filed: Jul. 18, 1991

Related U.S. Application Data

[63] Continuation of Ser. No. 549,189, Jul. 6, 1990, abandoned, which is a continuation-in-part of Ser. No. 377,652, Jul. 10, 1989, abandoned, which is a continuation-in-part of Ser. No. 275,475, Nov. 23, 1988, abandoned, which is a continuation-in-part of Ser. No. 142,447, Jan. 11, 1988, abandoned.

[51] Int. Cl.$^5$ .......................... A61K 37/02; C07K 7/10
[52] U.S. Cl. .................................... 514/12; 514/4; 514/13; 514/14; 514/15; 514/16; 514/17
[58] Field of Search ........................ 514/12-17, 4

[56] References Cited

PUBLICATIONS

Proceedings of the National Academy of Sciences, Cooper et al., vol. 84, pp. 8628–8632, Dec. 1987.
Proceedings of the National Academy of Sciences, vol. 84, Westermark et al., pp. 3881–3885, Jun. 1987.

*Primary Examiner*—Lester L. Lee
*Attorney, Agent, or Firm*—Lyon & Lyon

[57] ABSTRACT

The administration of antagonists and blockers of amylin or CGRP or both for the treatment of obesity and essential hypertension and associated lipid disorders and atherosclerosis.

12 Claims, 3 Drawing Sheets

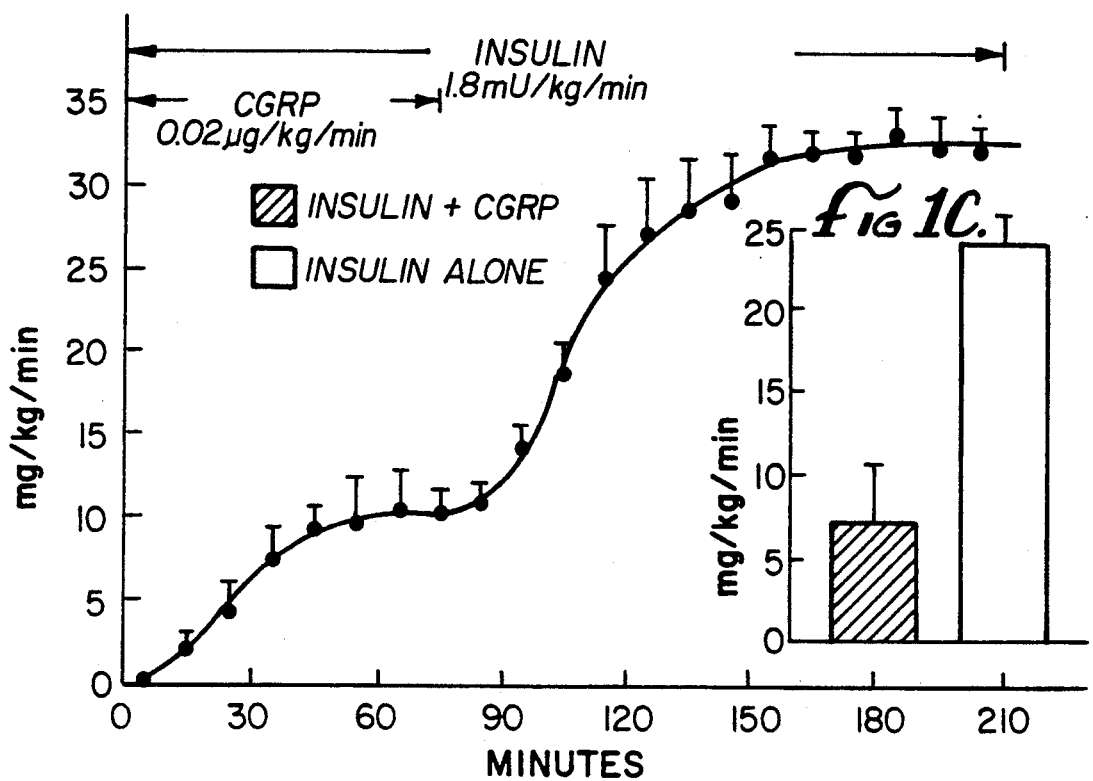
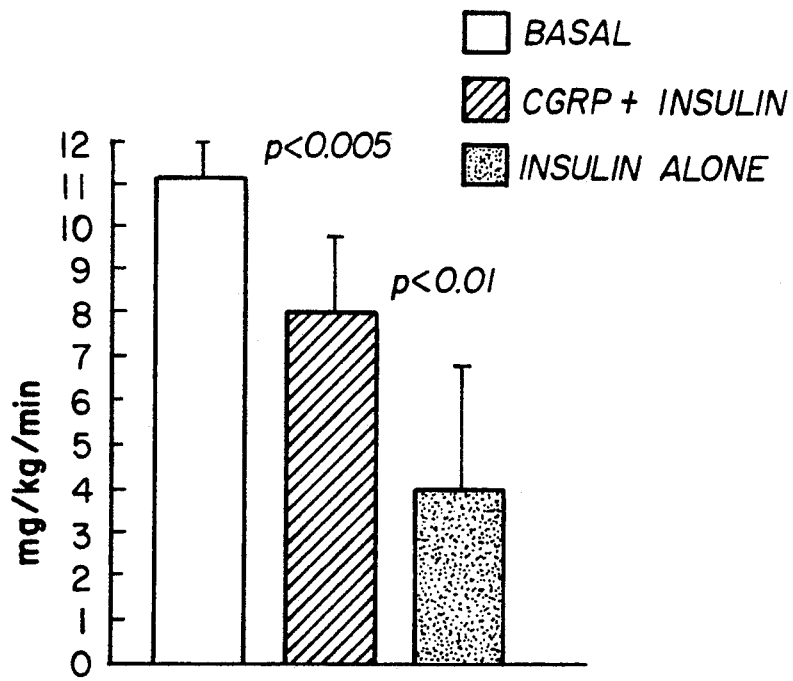

TREATMENT OF OBESITY AND ESSENTIAL HYPERTENSION AND RELATED DISORDERS

RELATED APPLICATIONS

This application is a continuation of U.S. application Ser. No. 549,189, filed Jul 6, 1990, now abandoned which is a continuation-in-part of U.S. application Ser. No. 377,652, filed Jul. 10, 1989, now abandoned which is a continuation-in-part of U.S. application Ser. No. 275,475, filed Nov. 23, 1988, now abandoned which is a continuation-in-part of application Ser. No. 142,447, filed Jan. 11, 1988, now abandoned, the contents of which are all hereby incorporated by reference.

BACKGROUND

1. Field of the Invention

The field of the invention is medicine, and more particularly, the effect of amylin antagonists and amylin blockers on glucose metabolism in peripheral tissues as a treatment for obesity and essential hypertension and associated lipid disorders and atherosclerosis.

2. Description of Related Art and Introduction of the Invention

Publications and other materials including patent applications used to illuminate the specification are incorporated herein by reference.

A 37-amino acid peptide called amylin has been isolated, purified, sequenced and characterized. The present invention discloses the use of amylin antagonists and amylin receptor blockers to control glucose and lipid metabolism for the treatment of obesity and essential hypertension and associated lipid abnormalities and atherosclerosis.

The peptide hormone amylin (previously termed "diabetes associated peptide") was isolated and characterized by Cooper et al. from the amyloid of the islets of Langerhans in Type 2 diabetics, and immunoreactivity to the peptide has been demonstrated in islet B-cells of both normal and Type 2 diabetic subjects. In view of our discovery that this hormone is derived from pancreatic amyloid masses, we have proposed the name "amylin".

Although it has been known for some time that amyloid masses in the islets of Langerhans are a feature of the pancreas in Type 2 diabetes, the monomer has only recently been shown to be the 37-amino acid peptide amylin (Cooper, G. J. S. et al., *Proc. Natl. Acad. Sci. USA* 1987; 84: 8628–8632), which has the following amino acid sequence:

```
1              5                 10
Lys—Cys—Asn—Thr—Ala—Thr—Cys—Ala—Thr—Gln—

11             15                20
Arg—Leu—Ala—Asn—Phe—Leu—Val—His—Ser—Ser—

21             25                30
Asn—Asn—Phe—Gly—Ala—Ile—Leu—Ser—Ser—Thr—

31             35
Asn—Val—Gly—Ser—Asn—Thr—Tyr—NH2
```

Specific immunoreactivity to amylin is found in islet amyloid, and in cells of the islets of Langerhans, where it co-localizes with insulin in the islet B-cells (see: Cooper, G. J. S. et al., *Lancet* ii: 966 (1987)). We have shown that the native amylin molecule contains a disulfide bridge between the Cys residues shown at positions 2 and 7 and is amidated at its 3' end. Both of these post-translational modifications are necessary for the complete biologic activity of amylin.

Insulin resistance is a major pathophysiological feature in both obese and non-obese type 2 diabetics, and was previously believed to be due mainly to a post-binding defect in insulin action (see: Berhanu et al., *J. Clin. Endoc. Metab.* 55: 1226–1230 (1982)). Such a defect could be due to an intrinsic property of peripheral cells, or caused by a change in concentration of a humoral factor in plasma, or both. Previous attempts at demonstrating a humoral factor responsible for insulin resistance have yielded conflicting results. Nor has it been possible to demonstrate an intrinsic post-binding defect in insulin resistance in type 2 diabetes mellitus (see: Howard, B. V. *Diabetes* 30: 562–567 (1981); Kolterman, O. G. et al., *J. Clin. Invest.*: 68: 957–969 (1981)).

The mechanisms of insulin resistance in type 2 diabetes are complex. Evidence, gleaned mainly from studies on adipose tissue, was said to suggest that in the mildest cases, insulin resistance could be accounted for largely by a deficiency in numbers of insulin receptors on peripheral target cells, but that as the degree of fasting hyperglycaemia increases, a postreceptor defect of insulin action emerges and progressively increases in significance (see: Kolterman et al., supra). The impaired glucose tolerance accompanying insulin resistance in type 2 diabetes is believed to be caused largely by decreased glucose uptake in peripheral tissues, but incomplete glucose-induced suppression of hepatic glucose production has also been said to be implicated (see: Wajngot et al., *Proc. Natl. Acad. Sci. USA* 70: 4432–4436 (1982)). In both obese and non-obese type 2 diabetics, the insulin dose-response curve is shifted to the right and there is a marked decrease in the maximal rate of glucose disposal and of total-body glucose metabolism in type 2 diabetics compared with non-diabetic subjects (Kolterman et al., supra; De Fronzo, R. A. et al., *J. Clin. Invest.* 76: 149–155 (1985)).

The majority of the glucose in an oral glucose load in humans is utilized in the periphery where, quantitatively, the most important tissue is skeletal muscle (De Fronzo, R. A. et al., *J. Clin. Invest.* 76:149–155 (1985); Katz et al., *Diabetes* 32: 675–679 (1983)), and it has recently been shown that reduced clearance of glucose into skeletal muscle accounts for the bulk of the decrease in total body glucose uptake in type 2 diabetics (see: De Fronzo et al., supra). The in vivo decrease in insulin-mediated glucose disposal in type 2 diabetes is said to be caused mainly by a marked decrease in non-oxidized glucose storage, primarily in skeletal muscle, rather than by a major shift in glucose or lipid oxidation (Meyer et al., *Diabetes* 29: 752–756 (1980); Boden et al., *Diabetes* 32: 982–987 (1983)). The degree to which relative insulin deficiency contributes to the overall reduction in whole-body glucose clearance is unclear. Muscle glycogen synthesis has been shown to determine the in vivo insulin-mediated glucose disposal rate in humans (Bogardus et al., *J. Clin. Invest.* 73: 1185–1190 (1984)).

Weight gain requires an intake of energy that is greater than its expenditure. It therefore follows that obesity occurs in response to sustained caloric intake in excess of requirement. Food intake need not be abnormally high during the development of obesity, provided activity is limited, although the development of obesity is normally accompanied by a high caloric intake. Once attained, the obese state is commonly maintained at a level of caloric intake insufficient to produce obesity, said to happen because accompanying morbidity prevents exercise (Foster, D. W. In: Wilson, J. D. & Foster, D. W., eds. Williams Textbook of Endocrinology. 7th ed. Saunders, Philadelphia, 1985: 1081-1107).

Obese patients frequently claim that they gain weight on amounts of food that do not cause obesity in other persons, perhaps due to a more efficient use of ingested calories than would be the case in lean individuals. Conversely, some persons can maintain weight near normal despite wide swings in the amount of food eaten (Black, D. et al., J. R. Coll. Phys. Lond. 1983; 17: 5-65). The excess calories necessary to gain weight vary considerably even among normal subjects; for example, in one study, individuals on a high fat diet required between 4703 and 8471 kcal/kg to gain 1 kg (Goldman, R. F. et al. In: Bray, G. A., ed. Obesity in perspective. DHEW Publication No. (NIH) 75-708. Washington, D.C.: U.S. Government Printing Office, 1975: 165-186). Numerous experimental findings support a difference in metabolic efficiency between lean and obese, the former apparently having the ability to waste calories as heat not shared by the latter. Observations in genetically obese rodents also support this notion, as these rodents have a defect in theromoregulation on exposure to cold (Trayhurn, P. et al. Theromoregulation in genetically obese rodents: the relationship to metabolic efficiency. In: Festing, M. W. F., ed. Animal Models of Obesity. New York: Oxford University Press, 1979: 191-203). Since ingested energy can be utilized for work, heat generation, or energy storage, it follows that the greater the conversion of excess calories to heat, the lesser will be their availability for storage as fat, given a fixed requirement for work.

On the basis of animal studies, it has been proposed that the propensity to develop obesity is genetically influenced through alterations in thermogenic capacity (James, W. P. T. & Trayhurn, P. Lancet 1976; 2: 770-773; James, W. P. T. & Trayhurn, P. Br. Med. Bull. 1981; 37: 43-48; Coleman, D. L. Nutr. Rev. 1978; 36: 129-132). The idea is that, in the past, when food supply was intermittent, genetic pressure would favor an efficient metabolism, so that a high percentage of food eaten would be stored for periods when food was not available. This genetic property would then manifest as obesity when food was constantly available.

Experimental evidence for this theory has been provided by experiments with the children of obese parents, which were based on the observation that obese children frequently have obese parents. Numerous metabolic indices indicated that the children of the obese have more efficient metabolisms, and that, early on, they may control their weight by restricting their food intake (i.e. eating physiologically) (Griffiths, M. & Payne, P. R. Nature 1976; 260: 698-700). In persons with established obesity, it has been said that there is probably a defect in glucose-induced (post prandial) theromogenesis, presumably as a result of insulin-resistance, but the defect is relatively small (Golay, A. et al. Diabetes 1982; 31: 1023-1028).

Hypertension, obesity and glucose intolerance (impaired glucose tolerance and type 2 diabetes mellitus) are associated in both clinical and epidemiological studies (Chiang et al., Circulation 403-421 (1960); Sims, E. A. H. Hypertension 4 (Suppl. 3); 43-49 (1982); Bray, G. A. Dis. Mon. 26: 1-85 (1979); West, K. M. Epidemiology of Diabetes and its Vascular Lesions. Elsevier/North Holland, New York, pp. 191-284, 351-389 (1978); Medalie et al., Arch. Int. Med. 135: 811-817 (1975); Zimmett, P. Diabetologia 22: 399-411 (1982); Barrett-Connor, M. Am. J. Epidemiol. 113: 276-284 (1981); Jarrett et al., Int. J. Epidemiol., 7:15-24 (1978); Butler et al., Am. J. Epidemiol. 16, 971-980 (1982) and may have common pathogenetic mechanisms (Modan et al., J. Clin. Invest. 75: 809-817 (1985)).

There are two major and distinct syndromes of hypertension in diabetes mellitus, essential hypertension and hypertension accompanying diabetic nephropathy (see respectively: Sleight, P. Essential Hypertension. In: The Oxford Textbook of Medicine. Weatherall, D. J. et al., eds. Oxford University Press, Oxford (1987); Magili et al., N. Engl. J. Med. 318: 146-150 (1988)). Over 50% of patients presenting clinically with type 2 diabetes mellitus have essential hypertension, i.e. elevated arterial blood pressure not secondary to an established primary cause of hypertension. Essential hypertension should be distinguished from the hypertension that frequently develops during the course of type 1 and type 2 diabetes, which is usually related to the onset and progression of diabetic nephropathy, and is therefore a secondary, renal form of hypertension, although the possibility of an inherited predisposition to raised arterial pressure in this condition has also been suggested (Magili et al., supra). The latter form of hypertension is accompanied by biochemical evidence of progressive nephropathy (i.e. microalbuminuria, elevated serum creatinine, etc.) and can thus be distinguished from essential hypertension not accompanied by nephropathy.

Insulin resistance is a major feature common to essential hypertension, obesity and type 2 diabetes. This insulin resistance occurs primarily in skeletal muscle, and results mainly from depressed rates of glycogen synthesis (nonoxidative glucose storage). Recent evidence confirms that essential hypertension is an insulin resistant state (Ferrannini et al., N Engl. J. Med. 317: 350-357 (1987); Shen, D.-C. et al., J. Clin. Endoc. Metab. 1988: 580-583 (1988)). The insulin resistance involves glucose but not lipid or potassium metabolism, is located in peripheral tissues, is limited to nonoxidative pathways of intracellular glucose disposal (primarily glycogen synthesis), and is directly correlated with the severity of the hypertension. It has also been demonstrated that the bulk (more than 70%) of glucose uptake in the whole body occurs in skeletal muscle (De Fronzo, R. A. & Ferrannini, E. Diabetes/Metabolism Reviews 3: 415-459 (1987)). In type 2 diabetes, it is primarily insulin resistance in skeletal muscle that is said to account for the low rates of glucose clearance from the blood and, hence, to be a major determinant of impaired glucose tolerance (Kolterman, O. G. Diabetes/Metabolism Reviews 3: 399-414 (1987)). Therefore, a major common feature between essential hypertension, type 2 diabetes mellitus and obesity is insulin resistance in skeletal muscle. While we believe that elevated amylin levels are the cause of this insulin resistance in type 2 diabetes, it is our further determination that they also contribute to the disease state in essential hypertension and obesity.

SUMMARY OF THE INVENTION

The present invention is directed to the use of amylin or CGRP receptor blockers and antagonists as treatments for obesity and essential hypertension, and associated lipid disorders and atherosclerosis, whereby amylin or CGRP antagonists and blockers are utilized to decrease the action of amylin or CGRP, thereby reducing insulin resistance in tissues made resistant to insulin by the effects of amylin or CGRP, particularly skeletal muscle, smooth muscle and liver. The action of the amylin and CGRP blockers increases the uptake of glucose into skeletal muscle, smooth muscle and liver, especially by counteracting the effects of amylin to increase hepatic glucose output and to reduce the rate of hexose uptake into muscle and liver cells, and also by counteracting the effect of amylin to reduce the rates of incorporation of glucose into glycogen. This action reverses the effect of amylin or CGRP to promote the storage of energy as fat, and increases the amount of glucose transported into muscle and liver cells. Amylin blockers will therefore act as anti-obesity and anti-hypertensive agents, as should CGRP blockers. Such treatments can be formulated with acceptable pharmaceutical carriers in therapeutically effective amounts, by known techniques.

The 37 amino-acid peptide amylin has been shown to be a major component of the amyloid of the islets of Langerhans in type 2 diabetes. Specific amylin immunoreactivity has been demonstrated in islet amyloid and in islet B-cells from both type 2 diabetics and non-diabetics. We have discovered that there is a direct relationship between amylin and the pathogenesis of type 2 diabetes and associated insulin resistance.

The invention disclosed herein lessens the effect of amylin on glucose metabolism and hence lipid metabolism in mammalian tissues. Experimental results demonstrate the unexpected fact that amylin reduces the rate of glucose uptake into red skeletal muscle in vitro and in vivo, mainly by decreasing the rate of incorporation of glucose into glycogen—an effect seen in the skeletal muscle of type 2 diabetics. In muscles treated with amylin, there was no response to insulin at the concentration necessary for half-maximal stimulation in non amylin-treated muscles. The effects of amylin were seen even in the presence of very low concentrations of insulin. Amylin produced a 30 percent reduction in the basal rate of glycogen synthesis in the presence of a basil concentration (1 uU/ml) of insulin. In marked contrast, amylin had no effect on either the basal or the insulin-stimulated rates of formation of $CO_2$ or triacyglycerol in isolated adipocytes. The effect of amylin treatment in muscle could only be overcome by increasing the concentration of insulin to the supra-physiological level of 1000 uU/ml.

We have further determined that excess amylin produces insulin resistance and reduced glucose uptake in muscle and thereby functions to shunt chemical energy from muscle to the liver, to promote the synthesis and secretion of VLDL-lipid (very-low-density-lipoprotein), and thence the storage of energy as fat in adipose tissue. We have also discovered that hypertension, especially essential hypertension, and obesity, represent subtly different aspects of this same metabolic defect involving an interaction between amylin/CGRP and their receptors. We believe that this discovery explains the prevalence of mixed pathologic conditions (over one-half of type 2 diabetics, for example, suffer from essential hypertension at the time of presentation), the prevalence of lipid/lipoprotein abnormalities in all these conditions, and the route of their association with atherosclerosis. Our discovery further explains why control of blood pressure or blood glucose alone is insufficient to avoid the effects of excessive mortality from atherosclerosis in these conditions. A major effect of the described blockers and antagonists will be to be remove the hyperinsulinaemia and consequently decrease insulin levels to normal values thus preventing increased fatty acids synthesis.

BRIEF DESCRIPTION OF THE DRAWINGS

FIG. 2b indicates the effect of an infusion of CGRP in an anaesthetised rat under conditions of hyperinsulinaemic, euglycaemic clamp, in which insulin and CGRP were initially infused together, followed by cessation of the CGRP infusion. Similar results have been obtained with an infusion of amylin.

FIG. 3 indicates the effect of CGRP on hepatic glucose output in anaesthetised rats, under conditions of hyperinsulinaemic, euglycaemic glucose clamp. Error bars give standard error of the mean.

DETAILED DESCRIPTION OF THE INVENTION

Figure 1:
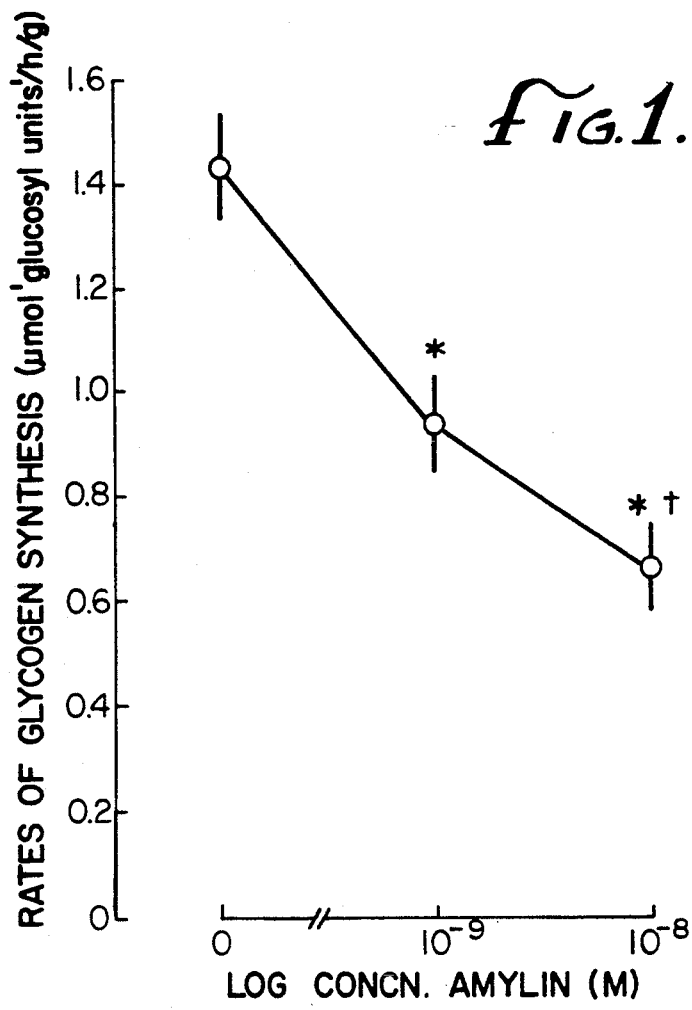
FIG. 1 indicates the effect of amylin on the insulin-stimulated fate of glucose uptake in isolated incubated skeletal muscles of the rat.

The novel peptide amylin, initially found in the amyloid masses in the islets of Langerhans in type 2 diabetes, causes insulin resistance in skeletal muscle and the liver. The neuropeptide CGRP (calcitonin gene-related peptide), which is present in a widespread nervous network throughout the body, including in skeletal muscle, shares this property.

Amylin is an amidated 37 amino-acid peptide which has strong homology with the CGRPs (Cooper et al., supra), and also has important homologies with the relaxins, insulin and the insulin-like growth factors (Cooper, et al., Progress in Growth Factor Research (1989); in the press). Recent studies now prove that amylin and CGRP are potent causative agents of insulin-resistance in skeletal muscle in vitro (Cooper, G. J. S. et al. Proc. Natl. Acad. Sci. USA 1988; 85: 7763–7766; Leighton, B. & Cooper, G. J. S. Nature 1988; 335: 632–635). This has also been demonstrated in vivo. Molina, M. et al., Diabetes 39:260–265 (1990). This has been shown both with synthetic amylin (Cooper et al., supra; Molina et al. supra) and with natural amylin extracted from diabetic pancreases (Leighton & Cooper, supra). We believe that the formation of islet amyloid is explained by excessive pancreatic production of amylin occurring in type 2 diabetes which, in turn, causes the tissues of these patients to become insulin resistant. We also believe that amylin is a factor in the causation of the essential hypertension and obesity which also accompany insulin resistance. This observation permits the development of substances which are active in the treatment of type 2 diabetes mellitus, obesity or essential hypertension, or combinations of these conditions.

Amylin acts by reducing both basal and insulin-induced uptake of glucose into skeletal muscle, especially by reducing the rate of incorporation of glucose into glycogen, and also by reducing the rate of glucose uptake into muscle cells (Molina, M. et al., *Science* 1989; submitted). In marked contrast, however, amylin does not influence either the basal or the insulin-stimulated rate of incorporation of glucose into either $CO_2$ or triglyceride in isolated adipocytes (Cooper, G. J. S. et al., Proc. Natl Acad. Sci. USA 1988; 85: 7763-7766). We have also demonstrated a direct relationship between the levels of CGRP-like immunoreactivity (using a CGRP and amylin cross-reacting antiserum) circulating in the blood and the severity of insulin resistance in type 2 diabetic humans. We have concluded that amylin causes the insulin-resistance in type 2 diabetes, probably in conjunction with CGRP and/or CGRP receptors.

Amylin promotes the incorporation of carbohydrate into long term energy stores as fat, whilst shunting it away from more immediate utilization in muscle. Amylin therefore acts to promote the storage of body-energy in adipose tissue, whilst reducing short-term energy-utilization in muscle, i.e. amylin can promote obesity and is a factor capable of increasing metabolic efficiency.

Figure 4:
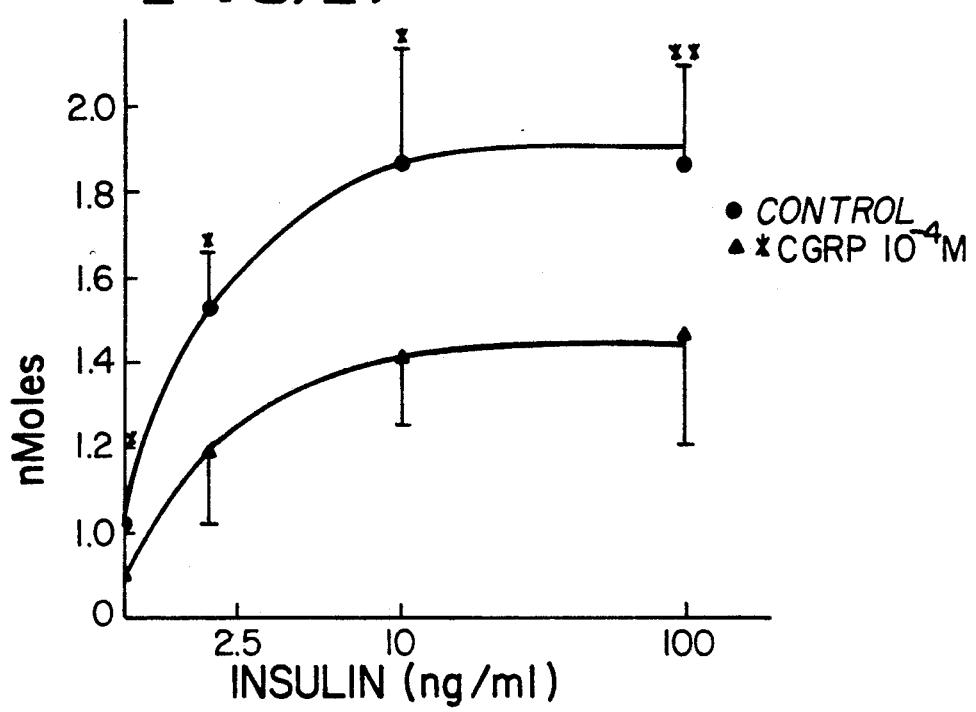
FIG. 4 indicates the effect of CGRP on insulin-stimulated glucose uptake in isolated BC3H-1 myocytes.

Recent studies in vivo, using CGRP and amylin infusions and the hyperinsulinemic, euglycemic glucose clamp method in anesthetised rats and conscious dogs, have provided confirmatory evidence that amylin and CGRP can produce insulin resistance in skeletal muscle, and have also shown that amylin and CGRP can produce resistance to the actions of insulin in the liver (Molina, M. et al., supra). This latter finding is important, as resistance to the actions of insulin is seen in type II diabetic patients. This group of studies also demonstrates that amylin and CGRP can produce insulin-resistance in skeletal muscle cells (see: FIG. 4; BC3H1 myocytes).

We have concluded that the amylin system functions to coordinate whole-body energy homeostasis by matching energy requirements (muscle energy utilization through modulation of the ACh signal at the motor end-plate) with the availability of energy in muscles through regulation of glucose uptake and glycogen synthesis. Accordingly, when amylin levels are raised in the body, muscles become insulin resistant and glucose uptake and energy availability in muscle falls while, at the same time, the ACh signal is reduced and muscle contractility is thereby reduced. This, in turn, provides an increasing energetic requirement that the body clear glucose by the only alternative route left open to it without becoming hyperglycemic. That route is the passing back to the liver of glucose and lactate, where they are converted into triglycerides, and thereby re-exported in the alternative form of VLDL-lipid, which is then transported to adipose tissue and stored as depot fat. This discovery appears to explain the association between conditions characterized by pathological insulin resistance, particularly in skeletal muscle and the liver (i.e.: type 2 diabetes mellitus, essential hypertension and obesity).

Relaxin, a molecule structurally related to amylin (Cooper et al., supra) reduces the blood pressure in spontaneously hypertensive rats (St. Louis, J. & Massicotte, G. *Life Sciences* 37: 1351–1357 (1985)). Relaxin is an ovarian polypeptide hormone (Bryant-Greenwood, G. D., *Endocrine Reviews* 3:62–69 (1982)), which has potent effects on uterine smooth muscle contraction (Bradshaw et al., *J. Reprod. Fert.* 63: 142–153 (1981), and which also modulates the release of oxytocin and vasopressin from the neurohypophysis (Dayanithi et al., *Nature* 325: 813–816 (1987)). In a single reported study, continuous intravenous infusion of purified rat relaxin was highly effective in reducing systolic blood pressure in spontaneously hypertensive (SHR) rats. The suggestion was made that, in these rats, relaxin is involved in the reduction or blood pressure during gestation.

We believe that molecules related to relaxin, such as amylin, interact with vascular smooth muscle contractility, either directly or via glycogen metabolism. Indeed, amylin may act as a natural antagonist of relaxin, or relaxin-like molecules.

We have devised a novel approach to detecting compounds having therapeutic potential in human hypertensive syndromes, especially essential hypertension and hypertension of pregnancy (HOP syndrome, EHP syndrome or pre-eclampsia), and in human obesity. The effect of amylin and relaxin on hypertension in the SHR rat is used as a model in which to examine the effects of putative therapeutic substances. Relaxin, amylin and CGRP act through modulating glycogen synthesis in skeletal and smooth muscle. Compounds having antihypertensive (as well as antidiabetic) properties are screened for by utilizing an amylin or CGRP inhibited, insulin-stimulated glycogen synthesis system, in order to detect substances capable of reversing insulin resistance. Useful compounds are then tested for efficacy in the SHR model. Compounds for use in the treatment of obesity are detected in the same fashion, and are then further tested in genetically obese rodents or other appropriate models. Of course, to the extent that amylin is a causative factor in hypertensive or obesity, it will be useful to beneficially block this unwanted action of amylin, and so improve blood pressure or obesity or both.

Compounds useful in the treatment of obesity and hypertension, and the lipid disorders and atherosclerosis associated therewith, include compounds and methods described in co-pending U.S. application Ser. No. 275,475, herein incorporated by reference, i.e., those which regulate the effect of amylin and/or CGRP and/or other amylin agonists, including biologically active sub-peptides of amylin or CGRP. These include the use of competitive inhibitors including substituted or altered peptides or sub-peptides or amylin or CGRP, and the regulation of the expression or production or release of amylin or CGRP, or active sub-peptides thereof. Chemical antagonists to amylin which bind to the amylin receptor without triggering a response are used to reduce the effects of amylin or amylin agonists (including CGRP) or biologically active sub-peptides thereof which act to inhibit basal and insulin-stimulated responses to glucose, or to prevent the interference of those molecules with insulin release. Thus, substituted $ser^2$, $ser^7$ peptides and sub-peptides of amylin and CGRP described in copending U.S. application Ser. No. 275,475, can ameliorate the effects of insulin resistance in skeletal muscle in individuals afflicted with obesity or essential hypertension, as can the partial antagonists amylin 8-37 and CGRP 8-37. Other competitive antagonists include cross-linked amylin agonists (including amylin, CGRP and active sub-peptides thereof), deamidated amylin, and amylin with incomplete disulfide bonding. Direct blockage of the amylin receptor can also be accomplished with monoclonal antibodies and anti-idiotype antibodies. Other chemical antagonists to amylin and amylin agonists include organic compounds which can be assayed and/or screened for anti-amylin effects by methods disclosed herein. Non-competitive amylin antagonists include antibodies directed to the active sites of amylin or CGRP.

The following examples are set forth to assist in understanding the invention, and should not, of course, be construed as specifically limiting the invention described and claimed herein. Such variations or the inventions which would be in the purview of those in the art, including the substitution or all equivalents now known or later developed, are considered to fall within the scope of the invention as hereinafter claimed.

EXAMPLES

Figure 2A:
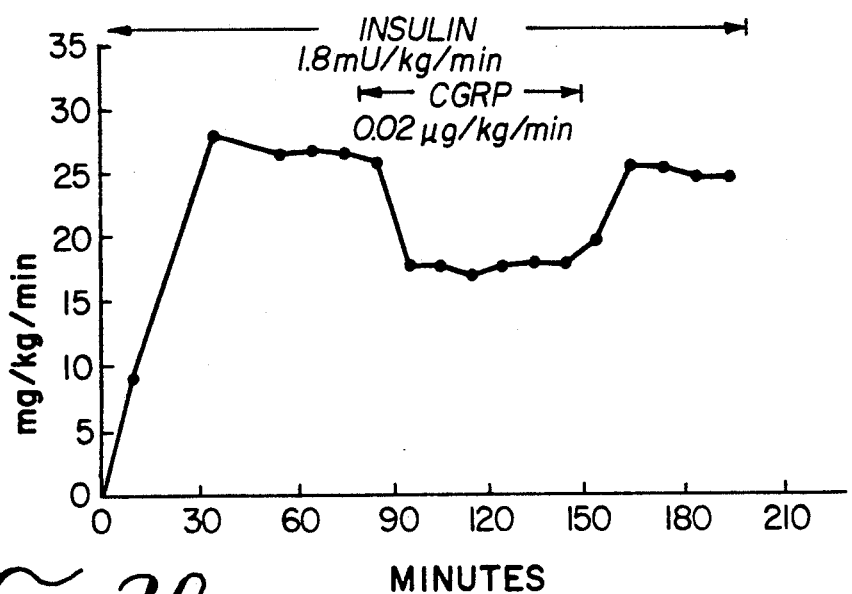
FIG. 2a indicates the effect of a CGRP infusion on glucose uptake in an anaesthetised rat under conditions of hyperinsulinaemic, euglycaemic glucose clamp, in which insulin alone was initially infused, following by insulin and CGRP. Similar results have been obtained with an infusion of amylin.

FIG. 2 demonstrates the results of hyperinsulinemic glucose clamp studies in rats infused with insulin (1.8 mU/kg/min or 0.064 ug/kg/min) and CGRP (0.02 ug/kg/min). FIG. 2A depicts a study in which insulin was infused at a constant rate for 210 minutes, with administration of CGRP from 80-150 minutes. Insulin led to a prompt increase in the glucose infusion rate necessary to maintain euglycemia to an insulin stimulated rate of $26.7 \pm 0.1$ mg/kg/min. Steady-state effects of insulin on glucose disposal were reached by 40-60 minutes. At 80 minutes the CGRP infusion was started and led to a prompt and marked decrease in the glucose infusion rate to a new steady state at a rate of $18.0 \pm 0.1$ mg/kg/min. After the CGRP effect was fully established and reached steady-state, CGRP infusion was discontinued (at 150 minutes) while insulin infusion was maintained. The glucose infusion rate promptly rose toward to original stimulated value.

An alternate protocol is portrayed in FIG. 2B in which CGRP (0.02 ug/kg/min) and insulin (1.8 mU/kg/min) were infused concomitantly at the outset for 75 minutes followed by insulin alone for 130 minutes. In these studies the mean steady-state glucose infusion rate was $9.9 \pm 0.3$ mg/kg/min during the CGRP plus insulin infusion. During the latter 60 minutes of the study when only insulin was administered, the mean peak glucose rose to an insulin stimulated value of $32.3 \pm 0.3$ mg/kg/min ($p<0.001$, CGRP+insulin vs. insulin alone).

It is evident that CGRP rapidly induces a marked state of in vivo insulin resistance, regardless of whether CGRP is given concomitantly with insulin or after the insulin effect was fully established. Furthermore, this effect is rapidly reversible upon withdrawal of CGRP.

In these experiments, the overall glucose disposal rate (GDR) equals the glucose rate plus hepatic glucose output (HGO). To assess GDR, 3H-glucose was infused during the studies depicted in FIG. 2B and GDR was measured in the basal state and over the last 20 mins of both the CGRP+insulin and insulin alone periods. Combining all studies, the basal GDR was $11.2 \pm 0.7$ mg/kg/min and rose by only $7.4 \pm 1.6$ mg/kg/min to 19.0 1.9 mg/kg/min with CGRP plus insulin compared to values of $24 \pm 0.9$ and $35.6 \pm 1.3$ mg/kg/min respectively with insulin alone (FIG. 1C). The mean steady-state plasma insulin level was $695 \pm 105$ uU/ml ($4.1 \times 10^{-9}$M) in the absence and $591 \pm 86$ uU/ml in the presence of the CGRP infusion (p=NS). Mean ($\pm$SE) CGRP values during the final 40 mins of the CGRP infusions were $4.6 \pm 1.3$ $10^{-8}$M. Dose response studies with CGRP showed no inhibition of insulin-stimulated GDR at a CGRP infusion rate of 0.005 ug/kg/min and an intermediate effect at an infusion rate of 0.01 ug/kg/min.

In addition to stimulation of peripheral glucose disposal, another important in vivo glucoregulatory effect of insulin is to inhibit HGO. FIG. 3 depicts the effects of CGRP and insulin on HGO during the clamp studies (depicted in FIG. 2B). Insulin alone suppressed HGO by 69% from $11.2 \pm 0.7$ to $3.9 \pm 2.7$ mg/kg/min, but in the presence of CGRP, insulin supressed HGO by only 29% to 8.0 mg/kg/min ($p<0.01$ insulin vs. insulin+CGRP). Thus, CGRP markedly antagonized the normal effect of insulin to inhibit HGO.

In vitro studies in isolated adipocytes and cultured BC3H-1 myocytes were also conducted. CGRP had no effect on either basal or insulin-stimulated 2-deoxyglucose uptake in adipocytes. Since 80-90% of in vivo insulin-stimulated glucose disposal represents skeletal muscle glucose uptake, an in vitro muscle cell system was also examined. As seen in FIG. 4, $10^{-8}$M CGRP significantly inhibited insulin-stimulated glucose uptake in cultured muscle cells at all insulin concentrations.

Having shown that CGRP can produce a state of insulin resistance in vivo, as well as in cultured myocytes in vitro, the CGRP levels in insulin resistant NIDDM subjects was examined. Fasting glucose, insulin, and CGRP levels were measured in a series of 8 control and 11 NIDDM subjects. The NIDDM group consisted of 6 males and 5 females with a mean age of $58 \pm 3$, and body mass index (BMI) of $29 \pm 2$ kg/M$^2$. The controls were 7 males mean age $45 \pm 4$ and BMI $23 \pm 1$ kg/M$^2$. As expected, fasting plasma glucose ($266 \pm 11$ vs. $91 \pm 2$ mg/dl) and serum insulin ($17 \pm 2$ uU/ml vs. $4 \pm 1$ uU/ml) levels were higher in the NIDDM subjects. An 3-fold mean elevation in serum CGRPLI in the NIDDM group was observed. This difference was highly statistically significant ($p>0.01$) and there was minimal overlap in measured values between normal and NIDDM subjects.

Figure 5:
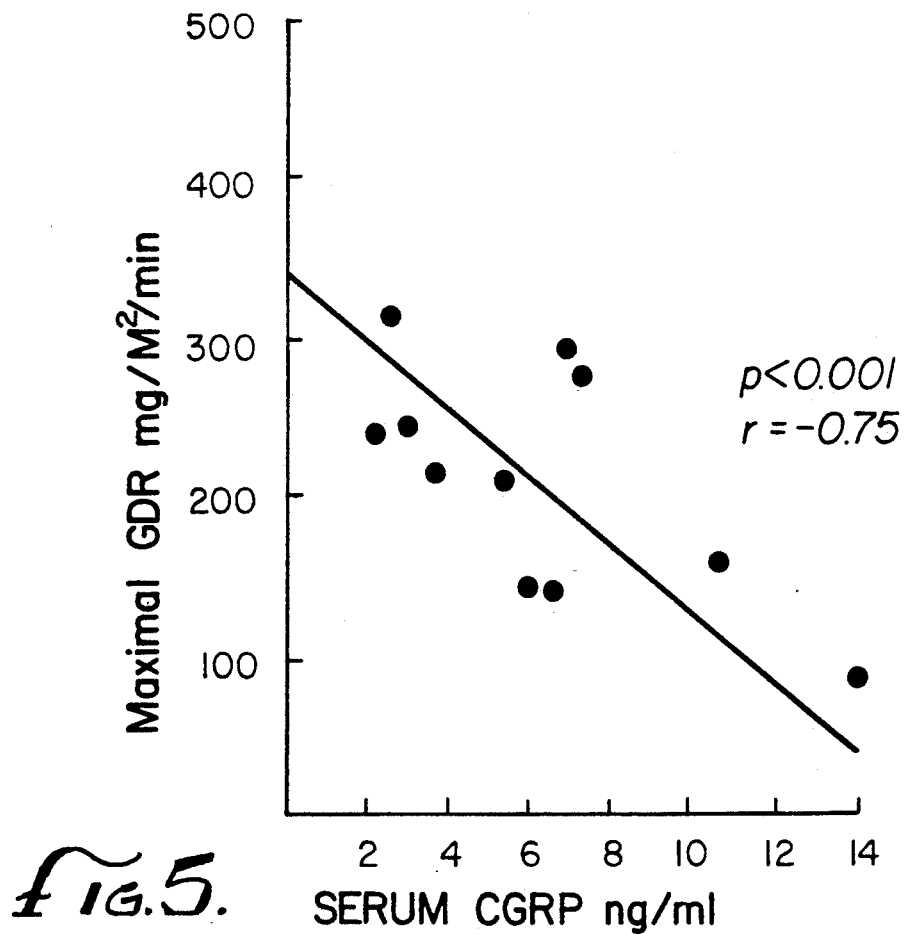
FIG. 5 indicates the relationship between maximal insulin resistance, as measured by maximal insulin-stimulatable glucose disposal, and levels of serum CGRP-like immunoreactivity in the blood of a group of insulin-resistant type 2 diabetic human patients.

To obtain a measure of insulin resistance in those subjects, euglycemic glucose clamp studies were performed at a maximally stimulating serum insulin concentration ($1160 \pm 67$ uU/ml). The GDR levels during the clamp studies were markedly reduced in the NIDDM group relative to controls ($458 \pm 22$ bs. $208 \pm 21$ mg/M$^2$/min, $p<0.001$). Among the individual NIDDM subjects, a correlation ($r=0.75$, $p<0.001$) existed between the GDR values and the fasting levels of CGRPLI (FIG. 5) such that the greater the degree of insulin resistance in these NIDDM subjects the higher the level of CGRPLI.

Similar results have been obtained using amylin. We have also shown that amylin acutely produces diabetes (fasting hyperglycemia greater than 140 mg/dL) when administered intravenously. Eight normal rats were injected with a 100 µg bolus of amylin (rat amylin, Bachem, Torrance, Calif.). An intravenous amylin bolus produced a profound hyperglycemia to diabetic levels within 15-30 minutes (usually around 200 mg/dL). This hyperglycemia persists for several hours. The hyperglycemia is partly accounted for by an increase in hepatic (endogenous) glucose output and partly by an increased impediment in peripheral glucose disposal. There is an increase in respiratory quotient (RQ) after amylin only when somatostatin is absent and insulin is allowed to increase in response to hyperglycemia. During somatostatin infusion (no endogenous insulin release), there is no change in RQ, indicating no change from lipid to carbohydrate fuel usage in response to amylin in the fasted animal.

In a further experiment we have shown that the amylin agonist CGRP 8-37 described in the related applications set forth above also functions as a partial amylin antagonist. Insulin was obtained as Humulin-R, 100 U/mL, recombinant human insulin (Eli Lilly, Indianapolis, Ind.). Amylin, obtained as rat amylin (Bachem, Torrance, Calif.) and 8-37 human CGRP (Bachem, Torrance Calif.) were also used. An antagonist assay was performed in vitro using the isolated soleus muscle from rats. It measured the rate of incorporation of radiolabelled glucose into muscle glycogen as follows: (1) under hormone-free conditions (zero insulin, zero amylin, zero hCGRP$_{8-37}$ [antagonist]); (2) under conditions of stimulation of glycogen formation with insulin (1000 µU/mL insulin, zero amylin, zero antagonist); (3) under conditions where the near maximal stimulation of glycogen formation has been inhibited with amylin (1000 µU/mL insulin, 20 nM amylin, zero antagonist); and, (4) under conditions where the suppression of glycogen formation by amylin has been disinhibited by an antagonist to the amylin action (1000 µU/mL insulin, 20 nM amylin, range of concentrations of antagonist [0, 1 nM, 10 nM, 100 nM, 300 nM, 1 µM, 10 µM]) There were therefore 9 treatment groups (conditions 1,2,3 and six subgroups of condition 4).

The right and left soleus muscles of 4-hour fasted rats were removed immediately after decapitation of the animals, divided in half and temporarily placed in physiological saline. Muscles were assigned to different treatment groups so that the 4 muscle pieces from each animal were evenly distributed among the 9 flasks representing the different assay conditions. Each flask contained 4 muscle pieces (replicates) bathed in 10 mL of Krebs-Ringer buffer+5.5 mM glucose, equilibrated with 95% $O_2$ and 5% $CO_2$ at 37° C. by passing a gas stream of this mixture over the surface of the continuously agitated warmed liquid. Pharmacologically active agents were added to the 10mL of medium to result in the above stated concentrations and mixtures. After a 30 minute "preincubation" period, 0.5 µCi of U-$^{14}$C-glucose was added to each flask and incubated for a further 60 minutes. Each muscle piece was then rapidly removed, blotted and frozen in liquid $N_2$, weighed and stored for subsequent determination of $^{14}$C-glycogen.

Frozen muscle specimens were digested in 1 mL 60% potassium hydroxide at 70° C. for 45 minutes. Dissolved glycogen was precipitated out by addition of 3 mL absolute ethanol and cooling to −20° C. overnight. The supernatant was aspirated and the glycogen washed with ethanol, aspirated and dried under vacuum. The remaining glycogen was redissolved in water and scintillation fluid and counted for $^{14}$C.

From a knowledge of the specific activity of $^{14}$C-glucose in the 5.5 mM glucose of the incubation medium, and the total $^{14}$C counts remaining in the glycogen extracted from each muscle, it was possible to determine the net rate of glycogen synthesis over the final 60 minute incubation period. This was normalized per mass of muscle and expressed as µmoles of glucosyl units incorporated into glycogen per hour per gram of muscle. The antagonist dose/response curve was fitted to a 4-parameter logistic model using a least-squares iterative routine (ALLFIT, v2.7, NIH, MD) to derive the $EC_{50}$ for disinhibition.

Results showed a 3.7 fold increase in rate of glycogen synthesis upon addition of 1000 µU/mL insulin to the media. This was decreased approximately 83% by the addition of 20 nM amylin. From this inhibited level, there was a dose-dependent return in incubation media. The increment in the rate of glycogen synthesis was up to about 115% and was half maximal at a CGRP$_{8-37}$ concentration of 1.2 nM (see FIG. 1). Thus, the peptide h-CGRP$_{8-37}$ partly reverses the inhibitory effect of amylin on insulin-stimulated muscle glycogen synthesis and may be regarded as an amylin antagonist.

Consistent with our discovery, another group has recently reported that amylin levels are elevated in obese patients with either impaired glucose tolerance or type 2 diabetes mellitus. Ludvik, B. et al., "Basal and stimulated plasma amylin levels in diabetes mellitus," Abstract No. 462, 50th Annual Meeting of the American Diabetes Association (Jun. 15-19, 1990, Atlanta, Ga.).

We claim:

1. A method for enhancing glycogen synthesis in a subject comprising administering to said subject an amount of an amylin antagonist effective to reduce amylin activity in said subject.

2. A method for the treatment of obesity in a subject comprising administering to said subject an amount of an amylin antagonist effective to reduce amylin activity in said subject.

3. A method for increasing the rate of incorporation of glucose into glycogen in mammalian muscle comprising administering to said mammal an amount of an amylin antagonist effective to reduce amylin activity in said mammal.

4. A method for the treatment of essential hypertension in a subject comprising administering to said subject an amount of an amylin antagonist effective to reduce amylin activity in said subject.

5. The method of any of claims 1, 2, 3, or 4 wherein said amylin antagonist is deamidated amylin.

6. The method of any claims 1, 2, 3, or 4 wherein said amylin antagonist is reduced amylin.

7. The method of any of claims 1, 2, 3, or 4 wherein said amylin antagonist comprises a biologically subactive subpeptide of amylin.

8. The method of any of claims 1, 2, 3, or 4 wherein said amylin antagonist is Ser$^2$ Ser$^7$ amylin.

9. The method of claim 7 wherein said amylin subpeptide comprises amylin 8-37.

10. The method of any of claims 1, 2, 3 or 4 wherein said amylin antagonist comprises a biologically subactive subpeptide of CGRP.

11. The method of any of claims 1, 2, 3 or 4 wherein said amylin antagonist comprises an anti-amylin antibody.

12. The method of claim 10 wherein said CGRP subpeptide comprises CGRP 8-37.

* * * * *